(12) United States Patent
Rauscher

(10) Patent No.: US 8,062,229 B2
(45) Date of Patent: Nov. 22, 2011

(54) METHODS AND DEVICES FOR MEASUREMENT AND TREATMENT OF PAIN AND THE TREATMENT OF INFLAMMATION AND OSTEOPOROSIS

(76) Inventor: Elizabeth A. Rauscher, Apache Junction, AZ (US)

( * ) Notice: Subject to any disclaimer, the term of this patent is extended or adjusted under 35 U.S.C. 154(b) by 867 days.

(21) Appl. No.: 11/837,397

(22) Filed: Aug. 10, 2007

(65) Prior Publication Data

US 2009/0043188 A1    Feb. 12, 2009

(51) Int. Cl.
  *A61B 19/00* (2006.01)
  *A61B 5/05* (2006.01)
  *A61N 1/00* (2006.01)
(52) U.S. Cl. ............. 600/557; 600/14; 600/409; 607/46
(58) Field of Classification Search .................. 600/409, 600/557; 607/46
  See application file for complete search history.

(56) References Cited

U.S. PATENT DOCUMENTS

| | | | |
|---|---|---|---|
| 849,653 A | 4/1907 | Bachelet | |
| 1,164,356 A | 12/1915 | Kaiser | |
| 2,517,325 A | 4/1947 | Lamb | |
| 3,841,305 A | 10/1974 | Hallgran | |
| 3,841,306 A | 10/1974 | Hallgran | |
| 4,056,097 A | 11/1977 | Maass | |
| 4,153,061 A | 5/1979 | Nemec | |
| 4,233,965 A | 11/1980 | Fairbanks | |
| 4,401,121 A | 8/1983 | Rodler | |
| 4,654,574 A | 3/1987 | Thaler | |
| 4,693,238 A | 9/1987 | Jenadek | |
| 4,723,536 A | 2/1988 | Rauscher et al. | |
| 4,889,526 A | 12/1989 | Rauscher et al. | |
| 6,113,552 A * | 9/2000 | Shimazu et al. | 600/557 |

FOREIGN PATENT DOCUMENTS

| | | |
|---|---|---|
| DE | 2707574 | 8/1978 |
| EP | 48451 | 3/1982 |
| EP | 0223354 | 9/2003 |

OTHER PUBLICATIONS

Bise et al., "Nonsuperconducting Systems for Detecting and Analyzing Low Intensity Pure Magnetic Field," Bull. Amer. Phys. Soc. 34, 125 (1989).
Rauscher et al., "Magnetic Control of Low Back Pain," Bull. Amer. Phys. Soc. 34, 125 (1989).
Rauscher et al., "Relaxation of Gauge Invariant Condition of ELF and VLF Phenomena and their Implications for Magnetic and Electronic Wave Transmissions," Bull. Amer. Phys. Soc. 34, 94 (1989).
Rauscher, "Completely Chaotic Systems and Complex Logic Equations," Bull. Amer. Phys. Soc. 34, 94 (1989).

(Continued)

*Primary Examiner* — Max Hindenburg
*Assistant Examiner* — Sean Dougherty
(74) *Attorney, Agent, or Firm* — Fish & Associates, PC

(57) ABSTRACT

A method for pain treatment and measurement according to various aspects of the present invention generally includes providing an external field to a portion of a living being, wherein the external field comprises a frequency of about 3040 Hz. This frequency of about 3040 Hz can also be intermixed with two or more other frequencies for the treatment and measurement of pain, and can be utilized alone or together with other intermixed frequencies to treat inflammation and osteoporosis.

31 Claims, 18 Drawing Sheets

OTHER PUBLICATIONS

Rauscher et al., "Magnetic Flux Control of Low Back Pain," Proceedings of the Association for the Advancement of Medical Instrumentation (AAMI), May 1989, p. 76, St. Louis.

Rauscher, "Pulsed Magnetic Field Control of Low Back Pain," Department of Physics and Astronomy Colloquium, Northwestern University, Mar. 10, 1993, Evanston, IL.

Rauscher et al., "Pulsed Magnetic Field Treatment and Chronic Back Pain," BEMS, European Bioelectromagnetics Association, Twenty Third Annual Meeting, Jun. 10-14, 2001, p. 5.

Rauscher et al., "Multiple Extremely Low Frequency Magnetic and Electromagnetic Field Effects on Human Electroencephalogram and Behavior," US National Institute of Enviromental Health Sciences, Tucson, AZ, p. 28.

Rauscher et al., "Degranulation of In Vivo Rat Brain Mast Cells by Exposure to External Pulsed Magnetic Fields," US National Institute of Enviromental Health Sciences, Tucson, AZ, p. 32.

Rauscher,"Healty, Healing, and Medicine" Tecnic Research Laboratory and Medicine Electronics, Oct. 1, 1985.

Rauscher,"Probing into Control Mechanisms in Cellular Healing Processes: San Francisco Initiative." Planetary Association for Clean Energy Newsletter, Feb. 1981, p. 8.

Becker, "New Light on Visualization." Cross Currents, Jeremy P. Tarcher, Inc. Los Angeles, pp. 104-106.

Wewers et al.,"A Critical Review of Visual Analogue Scales in the Measurement of Clinical Phenomena." Research in Nursing & Health, 1990, 13, 227-236.

Rauscher."Closed Cosmological Solutions to Einstein's Field Equations." Lawrence Radiation Laboratory, University of California, Berkeley, Cal., 1972, pp. 661-665.

Rauscher."Magnetic Field Interaction with Macro Biological Systems with Application to Effects on Physiology and Consciousness in Humans." International Conference on Energy Medicine, 1987, pp. 6-7.

Rauscher E A. "Response of Physiological Parameters to Low Frequency and Low Intensity of Pulsed Magnetic Fields." Ninth Annual International Symposium on Man and his Environment in Health and Disease, Feb./Mar. 1991.

Rauscher "Environmental Magnetic and Electromagnetic Field Monitoring, An Analysis of Field Effects on Biological Systems." Ninth Annual International Symposium on Man and his Environment in Health and Disease, Feb./Mar. 1991.

Rauscher "Response of Physioloical Parameters to Low Frequency and Low Intensity Pulsed Magnetic Fields and the Effect on Human Consciousness" The 31st Annual United States Psychotronics Conference, Jul. 2005, Columbus, Ohio.

* cited by examiner

BEATING (1 ms TRACE)

BURSTING (1 ms TRACE)

METHODS AND DEVICES FOR MEASUREMENT AND TREATMENT OF PAIN AND THE TREATMENT OF INFLAMMATION AND OSTEOPOROSIS

DESCRIPTION OF THE INVENTION

1. Field of the Invention

The present invention relates methods and devices for pain treatment and measurement, and the treatment of osteoporosis and inflammation.

2. Background of the Invention

Pain is a sensation in which a living being experiences discomfort, distress, or suffering due to provocation of sensory nerves. Pain can range from mild discomfort to intolerable agony. In most cases, pain stimuli, although sometimes necessary for warning about harm and proper reaction, are harmful to the body and tend to bring about maladaptive reactions by which the body attempts to protect itself from and results in reduced mobility, reduced functionality and reduced quality of life. Some physiological factors can be effected by the experience of pain such as increased blood pressure, suppression or imbalance of certain neurotransmitters, muscle atrophy, incorrect posture and many others.

Conventional methods for treating pain, such as through surgery and pharmaceuticals, often do not fully remedy chronic pain and their use may have undesirable consequences. Utilizing pharmaceuticals to treat pain, for example, may merely mask the pain temporarily, and may result in side effects such as addiction.

BRIEF SUMMARY OF THE INVENTION

A method for pain treatment and measurement according to various aspects of the present invention generally includes providing an external field to a portion of a living being, wherein the external field comprises a frequency of about 3040 Hz. This frequency of about 3040 Hz can also be properly intermixed with two or more other frequencies for treatment and measurement of pain, and can be utilized alone or together with other intermixed frequencies to treat inflammation and osteoporosis.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description serve to explain the principles of the invention.

BRIEF DESCRIPTION OF THE DRAWINGS

A more complete understanding of the present invention may be derived by referring to the detailed description and claims when considered in connection with the following illustrative figures.

Elements in the figures are illustrated for simplicity and clarity and have not necessarily been drawn to scale. For example, the dimensions of some of the elements in the figures may be exaggerated relative to other elements to help to improve understanding of the following description of the illustrated embodiments.

DETAILED DESCRIPTION OF EXEMPLARY EMBODIMENTS

The systems and methods introduced herein summarize exemplary embodiments of the present invention. Embodiments of the present invention may be described herein in terms of various functional blocks and processing steps. Such functional blocks may be realized by any number of hardware and/or software components configured to perform specified functions and achieve various results. For example, embodiments of the present invention may employ any desired machine, processor and/or integrated circuit component, interface, transmission media, integrated and/or distributed computer system, storage system, database, and the like, which may carry out any desired function under the control of one or more computers and/or other control devices. Additionally, the present invention may employ any number of conventional techniques for data storage and analysis, component interfacing, data processing, information conversion, communication, and the like. Furthermore, the present invention may be practiced in conjunction with any number of processes, systems, and/or devices.

Overview

Living tissue and living beings can operate in a biochemical, electromagnetic and mechanical manner. We can utilize these properties of living systems which may be are embodied in the device of this invention for the measurement and treatment of pain, inflammation reduction and the treatment of osteoporosis.

Endorphin and enkephalin production occur and receptors can be activated and then can be renormalized, which can reduce and eliminate pain. Proper levels of neurotransmitters and hormones can be found to occur when the proper emitter signals can be used to entrain the neuronal and other pathways.

Prostaglandin is any of a group of autacoids, which are not hormones, which can have physiological actions such as fluid balance, platelet aggregation, blood flow and neurotransmitter function and anti-inflammatory response. Inflammation can produce pain and can be associated with increased histamine production. These neurotransmitters can affect the hypothalamus and limbic system.

The body's piezoelectric response may be one of many informational channels of the human body which involves electrical, mechanical, biochemical and homodynamic processes, as well as musculature. Piezoelectricity is one of many such mechanisms of the human body.

Figure 1:
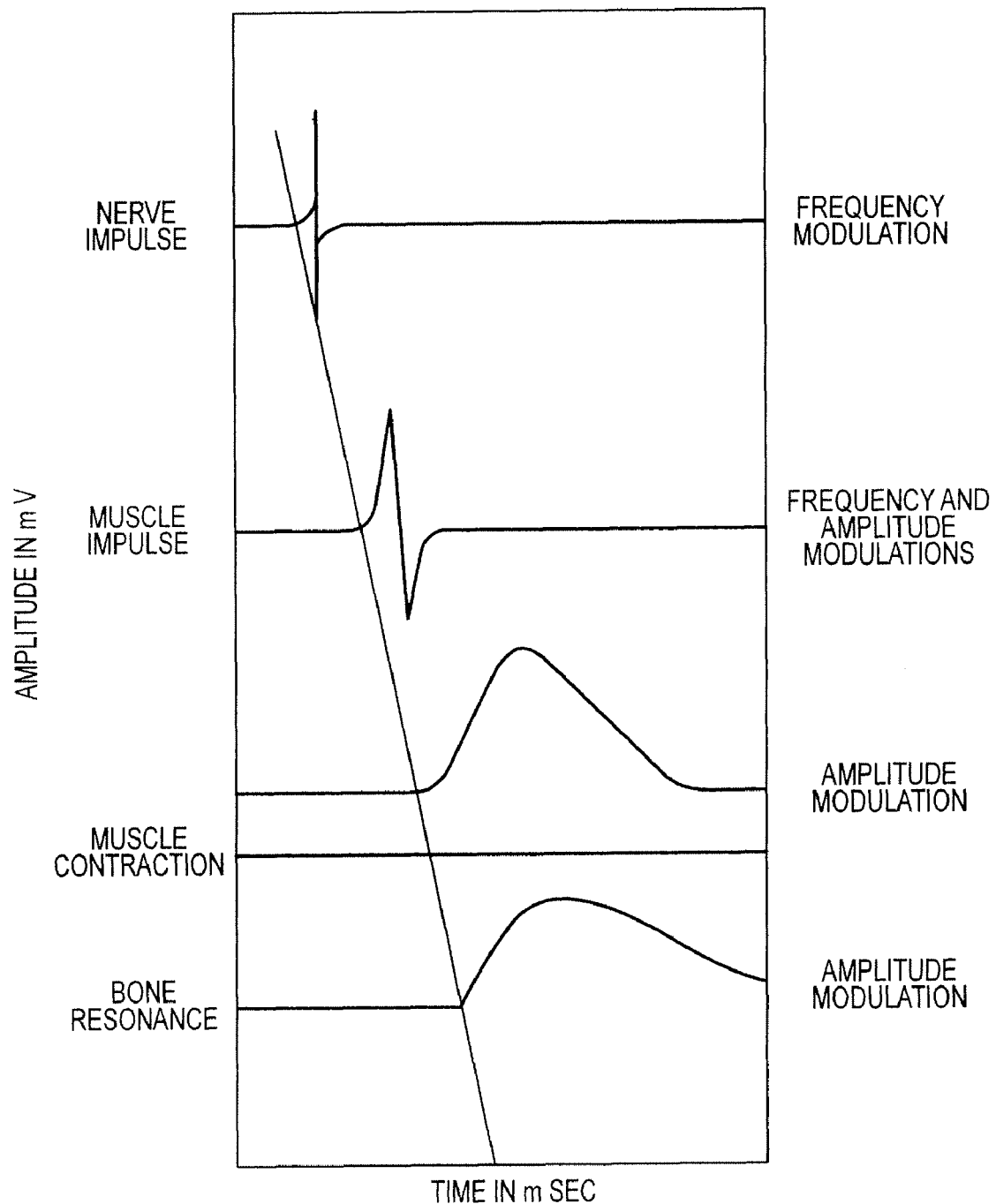
FIG. 1 is a graph of the time domain emissions of nerve, muscle and bone resonance tissue.

Different types of living tissue produce, transmit and receive different types of bioelectric fields. For example, referring to FIG. 1, the display in FIG. 1 is in the time domain, nerve impulses are of shorter duration, frequency-modulated impulses while bone produces longer duration, amplitude-modulated impulses. Muscle tissue can act in a frequency and amplitude modulated manner. A Fourier analysis of these fields displays their various frequency components.

Figure 2:
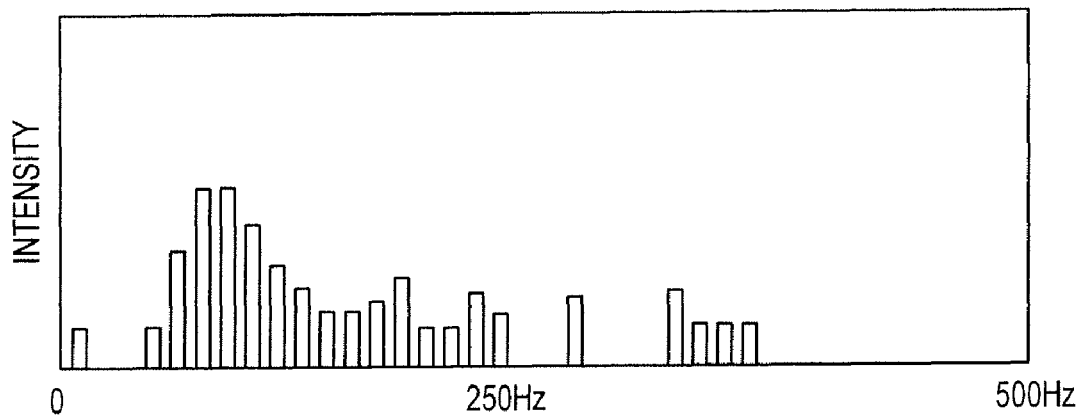
FIG. 2 is a graph of the Fourier frequency components generated by the right forearm of a healthy 48-year-old male.
Figure 3:
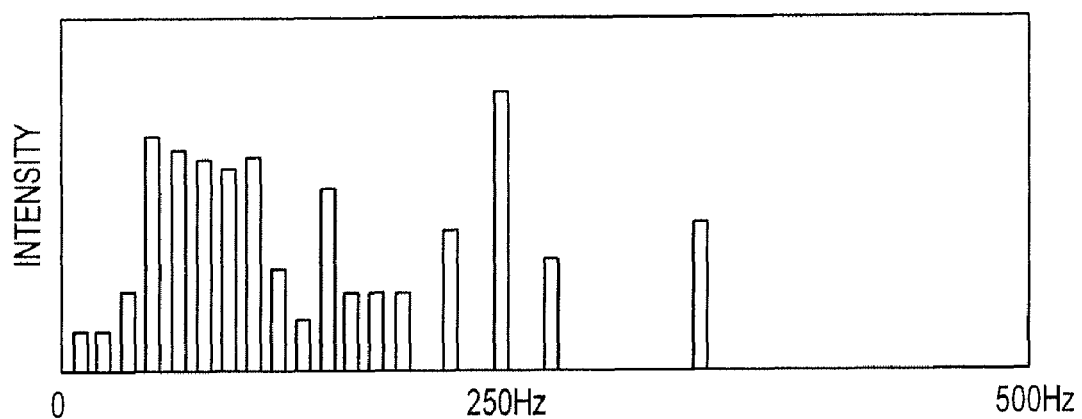
FIG. 3 is a graph of the Fourier frequency components generated by the left calf of a healthy 42-year-old male.
Figure 4:
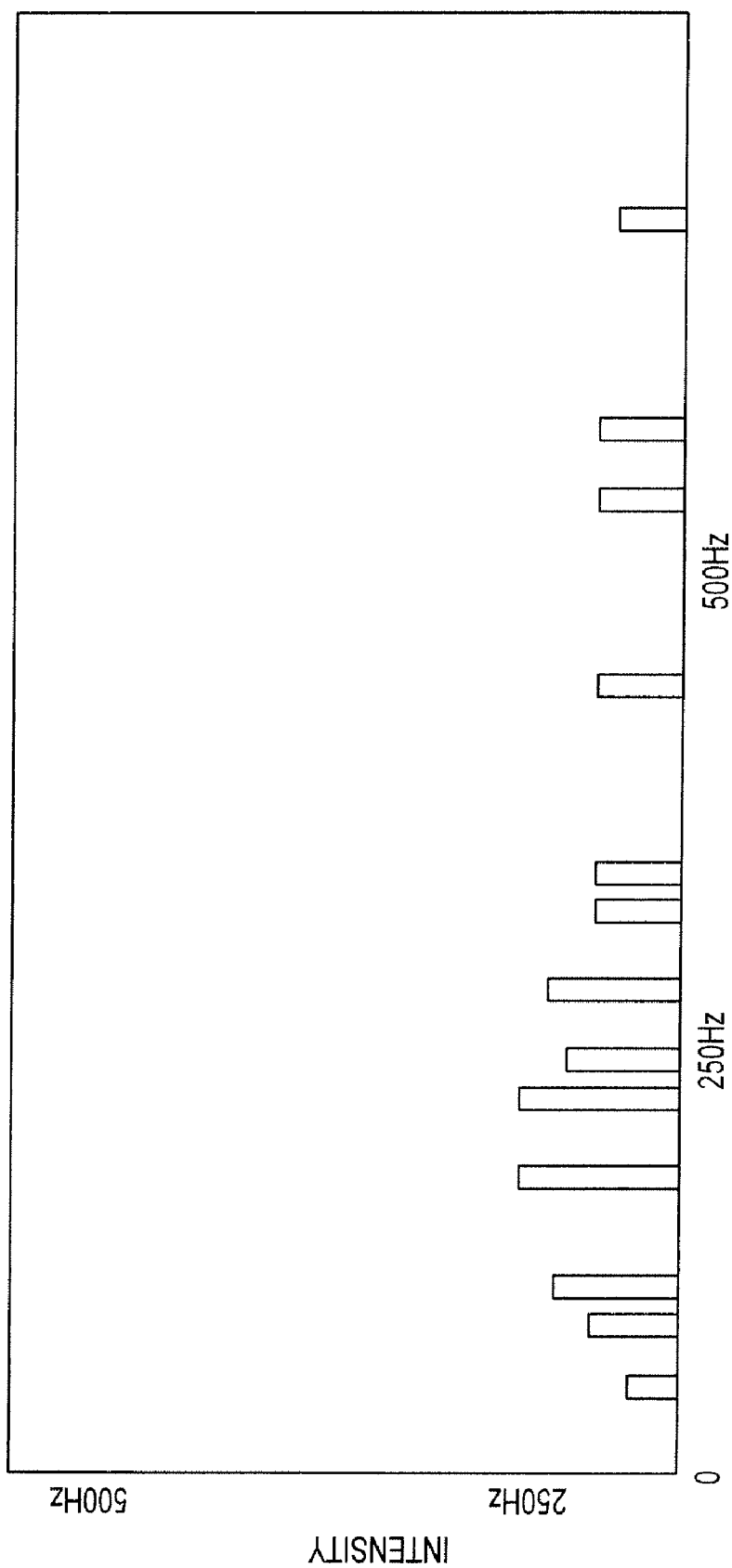
FIG. 4 is a graph of the Fourier frequency components generated by the arthritic right forearm of an 86-year-old female.

FIG. 2, for example, displays the Fourier frequency components of the field emitted by the right forearm of a healthy 48-year-old male. In FIG. 3, the Fourier components of a healthy 42-year-old male's left calf are displayed. Pain in a living being can be associated with missing information in the bioelectric fields produced by a living being. This missing information is marked by a decrease in the number and amplitude of Fourier frequency components in the bioelectric fields a being produces. For example, FIG. 4 displays the Fourier components generated from the arthritic right arm of an 86-year-old female. Compared to the fields generated by the healthy limbs in FIGS. 2 and 3, the relative amplitude and number of the Fourier components in FIG. 4 are substantially reduced in amplitude and the bandwidth becomes larger which can be in order to attempt to compensate for the lost information. This compensation is inadequate as these higher frequency components are usually of low amplitude. By exposing the tissue of a living being that emits a field having missing and/or reduced-amplitude Fourier components to an external electromagnetic or magnetic field according to various aspects of the present invention, the bioelectric field emitted by the tissue may be re-trained to emit the previously missing and reduced components, eliminating the pain associated with and in the tissue. The Fourier frequency output from the human body appears to remain normalized after treatment as the pain is eliminated. However, this is not the only method of pain reduction or other benefit of the present invention. Pain relief can occur due to the renormalization of neuronal pathways in the brain, central nervous system and peripheral nervous system and acts to replace and correct missing and distorted signals in various tissues in which pain receptor and other signaling occurs.

Operation

In one embodiment of a method for treating pain according to various aspects of the present invention, a precisely tuned external field that mimics the field of properly-functioning tissue may be exposed to a living being in order to eliminate pain.

Figure 5:
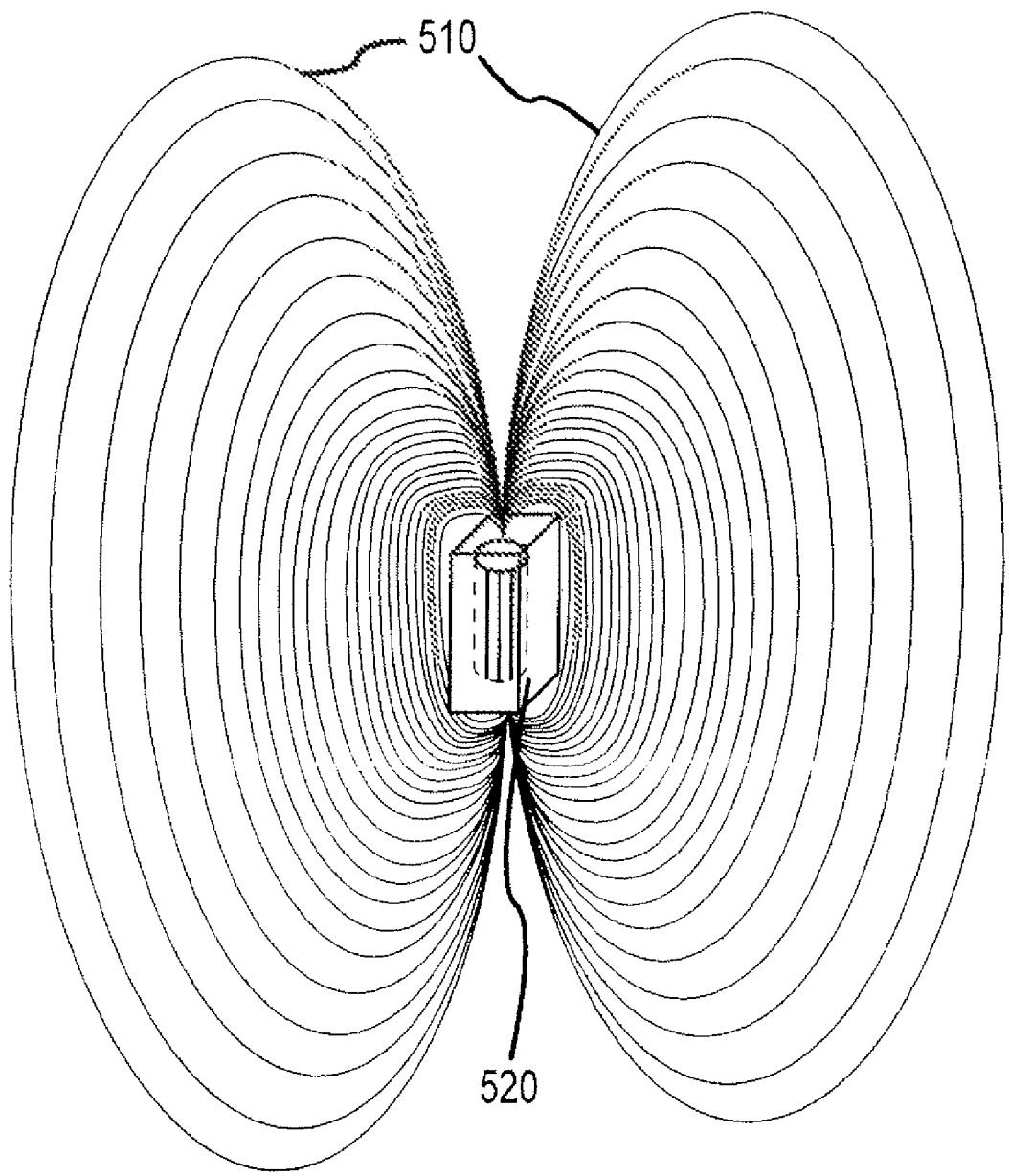
FIG. 5 is a diagram depicting an exemplary magnetic field generated by a device according to various aspects of the present invention.

Any appropriate type of field may be used in conjunction with the present invention, such as a magnetic and electromagnetic fields. In one exemplary embodiment according to various aspects of the present invention, referring to FIG. 5, an external magnetic field 510 is generated by an inductive coil 520. The external field 510 may be of any suitable magnitude. In one embodiment of the present invention, for example, an external field 510 for treating pain may have a magnitude of 5.5 Gauss or higher. The magnitude of the field may be modified in any manner for any desired purpose, such as to analyze the reaction of a patient to the change in the magnitude of the field in order to determine the patient's level of pain. For the treatment of osteoporosis, the field strength can be approximately ten times the magnitude for pain reduction treatment and the treatment regime can be about four to eight times as long for pain reduction and elimination. Another treatment regime may be employed in combination with the present invention to treat pain, osteoporosis, inflammation or other medical conditions.

Figure 6:
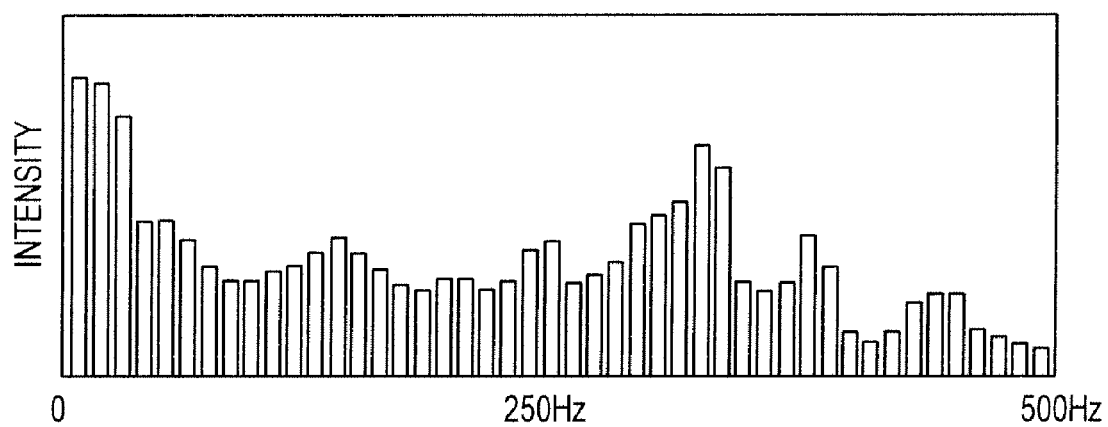
FIG. 6 is a graph of exemplary Fourier frequency components generated by a device according to various aspects of the present invention.
Figure 7:
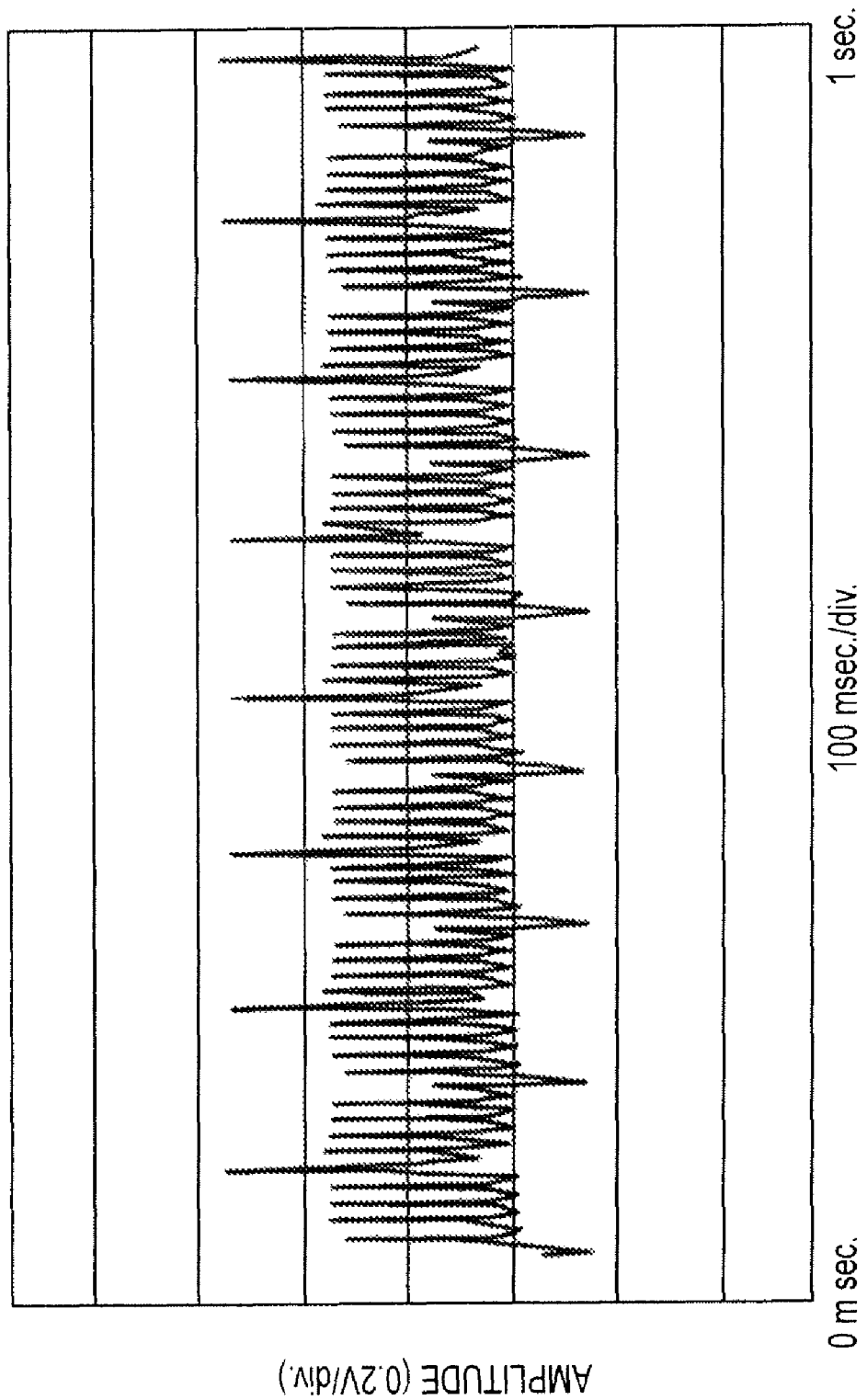
FIG. 7 is a graph depicting an exemplary waveform of intermixed frequencies generated by a device according to various aspects of the present invention.
Figure 8A:
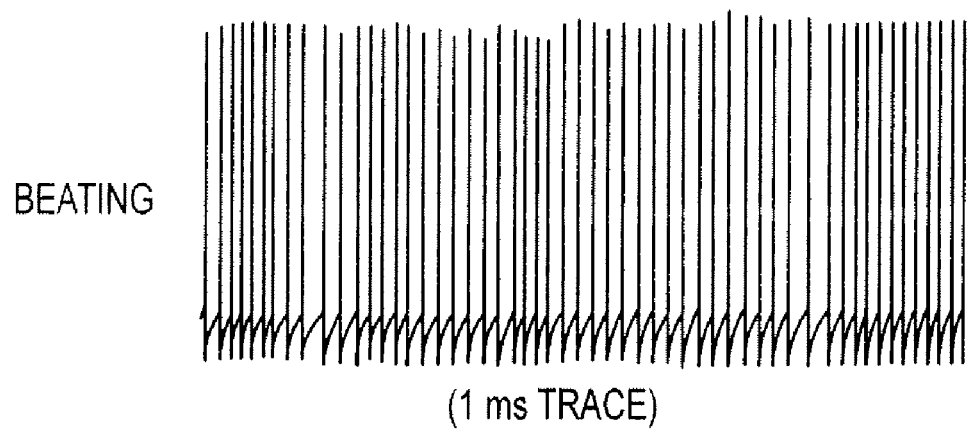
FIG. 8 depicts the waveforms patterns typical of endogenous neuronal electrical activity.
Figure 8B:
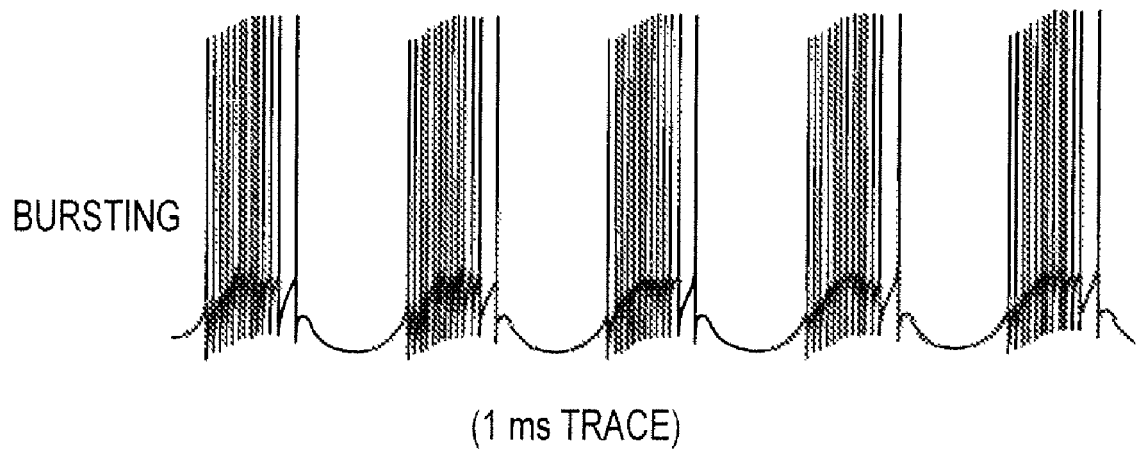

The field 510 may be configured to match any suitable biological process, tissue, and the like. For example, referring to FIG. 1, the amplitude and frequency characteristics of the field 510 may be generated to correspond with the type of tissue being treated. FIG. 6, for example, displays a field 510 generated according to various aspects of the present invention in order to mimic the number and amplitude of Fourier frequency components characteristic of healthy tissue. For example, FIG. 7 displays the waveform generated by a system of four inductive coils that may be used to replace the missing Fourier components in arthritic tissue or any other tissues producing pain. The output is the 22.8 Hz intermix output comprising a 7.6 Hz signal and a 70.25 Hz signal. Additionally, the field 510 may be generated to match patterns of endogenous electrical activity from neuronal processes. Referring now to FIG. 8, Neuronal processes beat and burst in a regular manner. The trace speed is for a 1 m sec. trace. The neuronal beating and bursting characteristics of a living being may be mimicked by the waveform of the field 510 generated according to aspects of the present invention.

Figure 9:
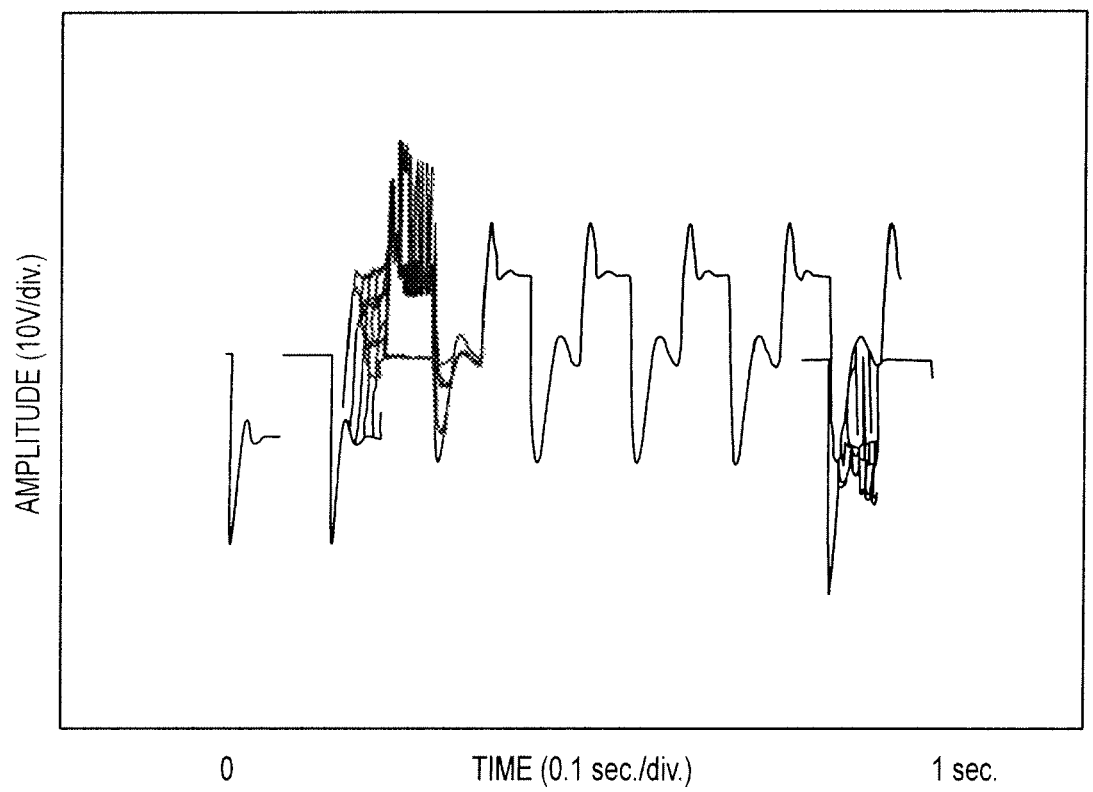
FIGS. 9, 10A, 10B, 11, 12A, and 12B are graphs depicting exemplary waveforms of intermixed frequencies according to various aspects of the present invention.
Figure 10A:
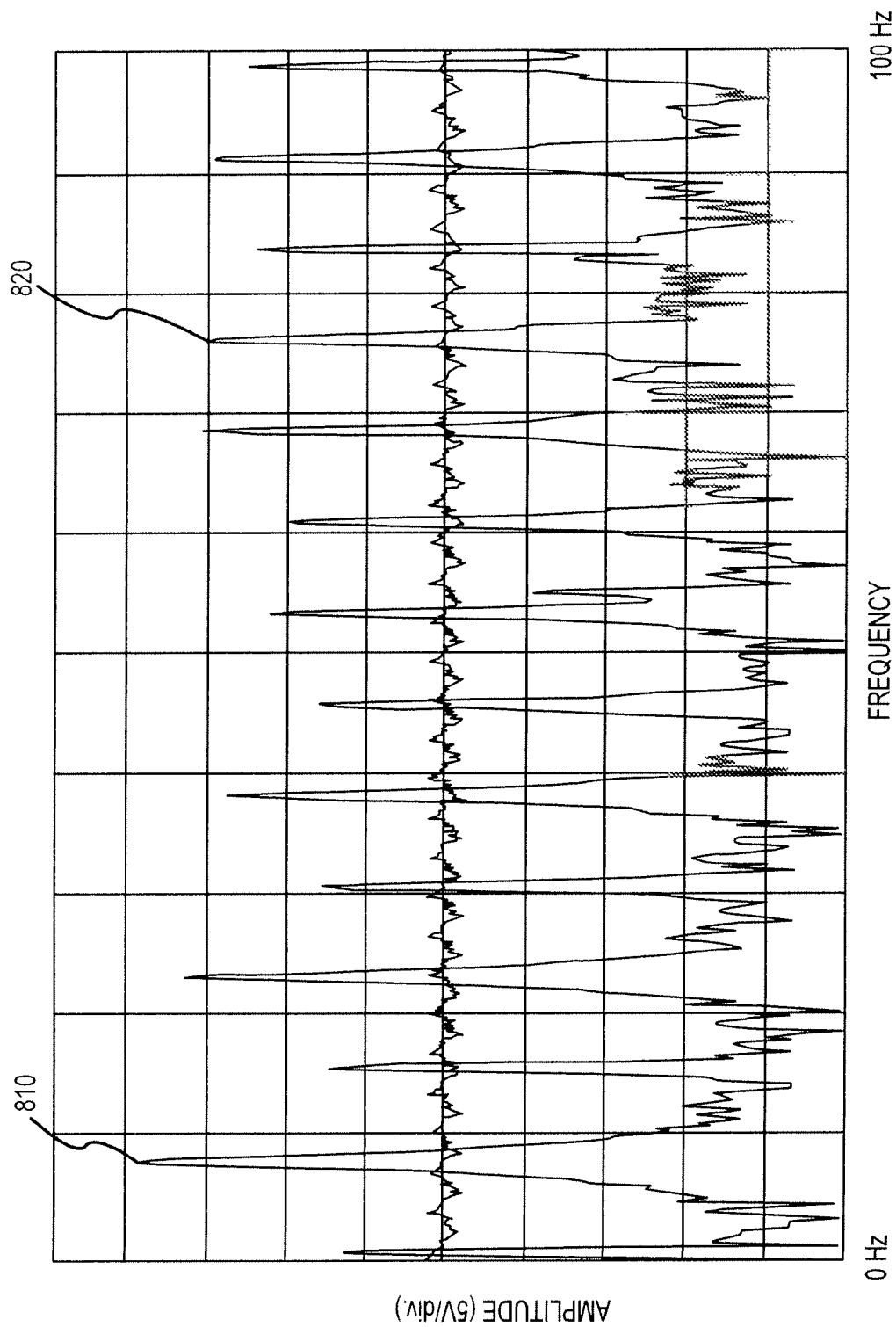
Figure 10B:
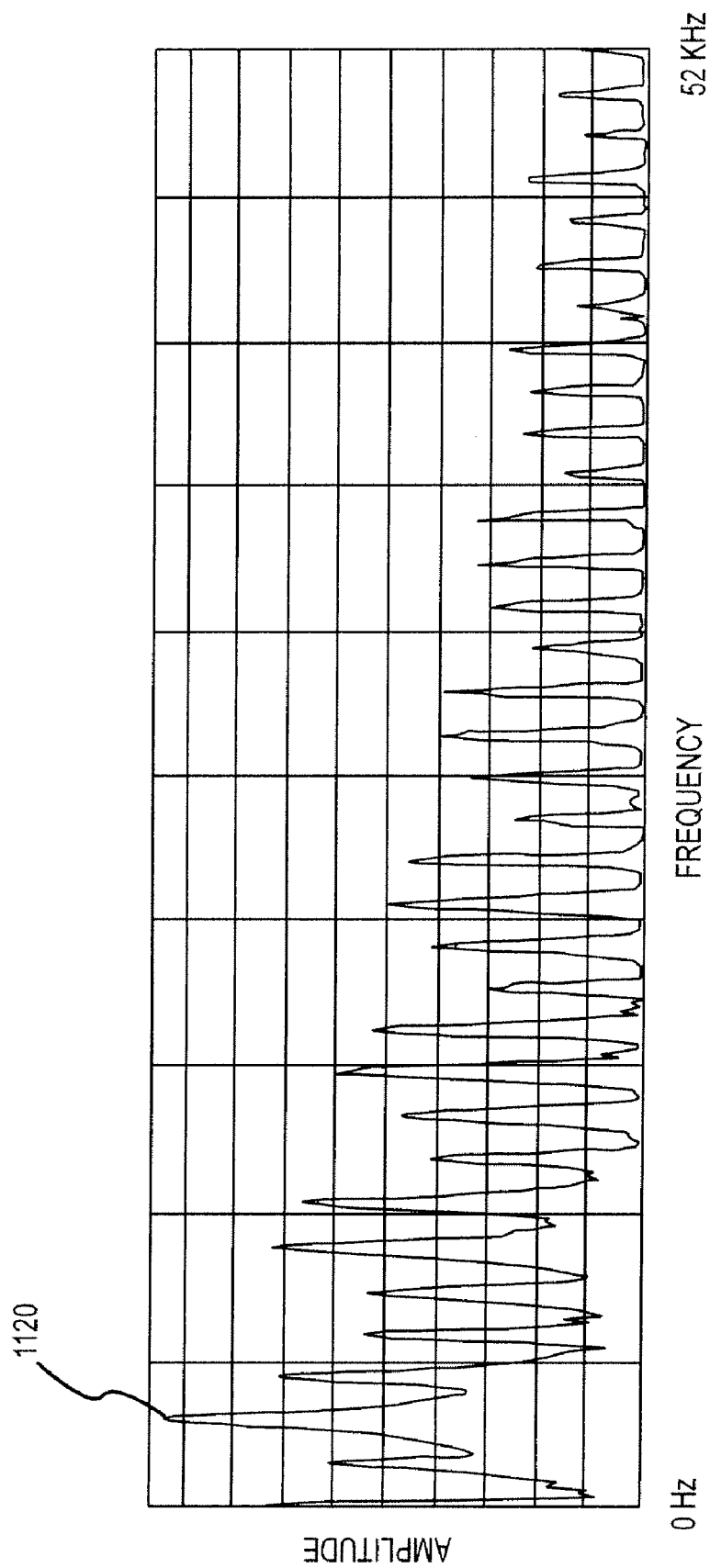
Figure 11:
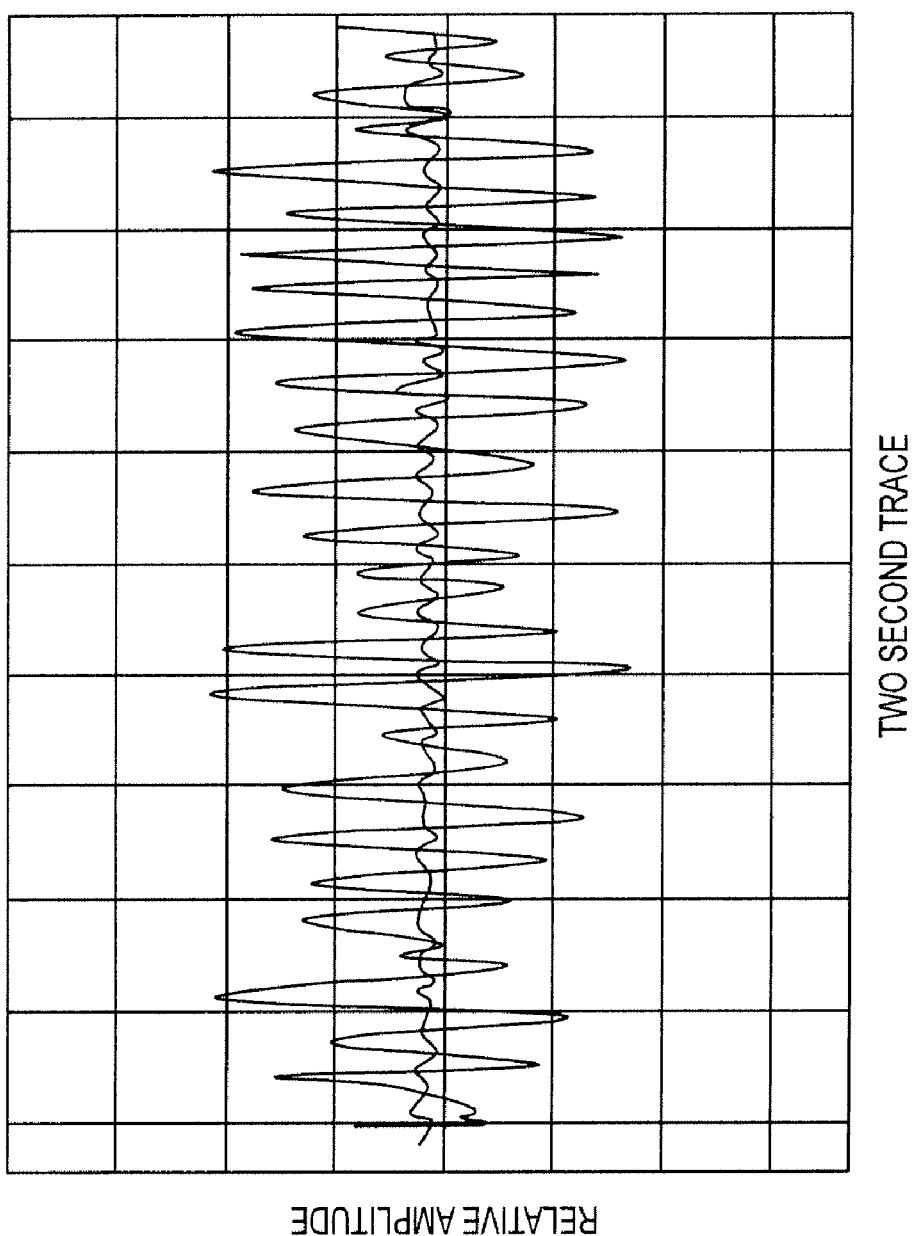
Figure 12A:
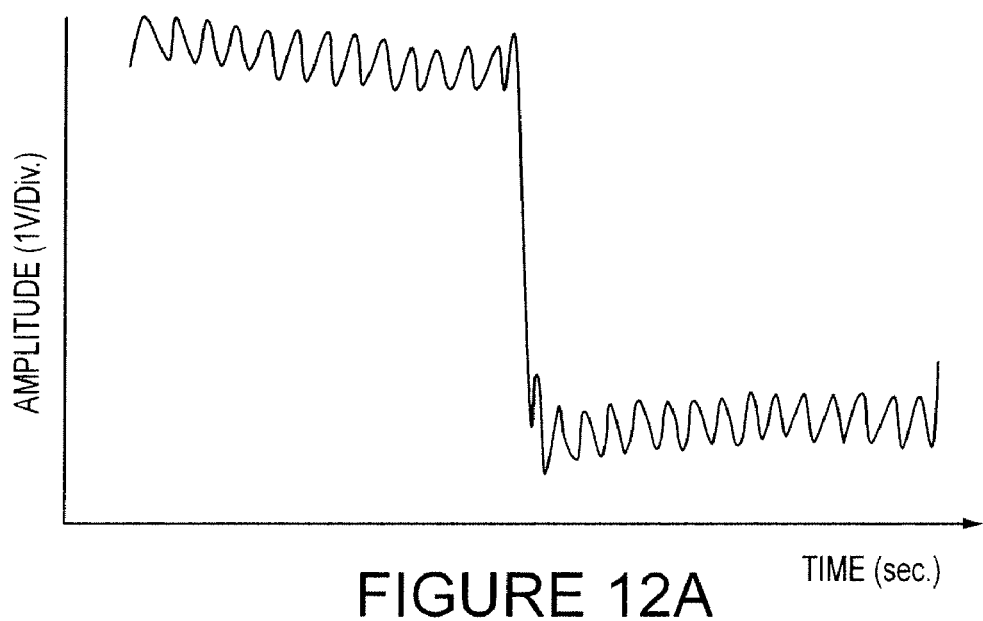
Figure 12B:
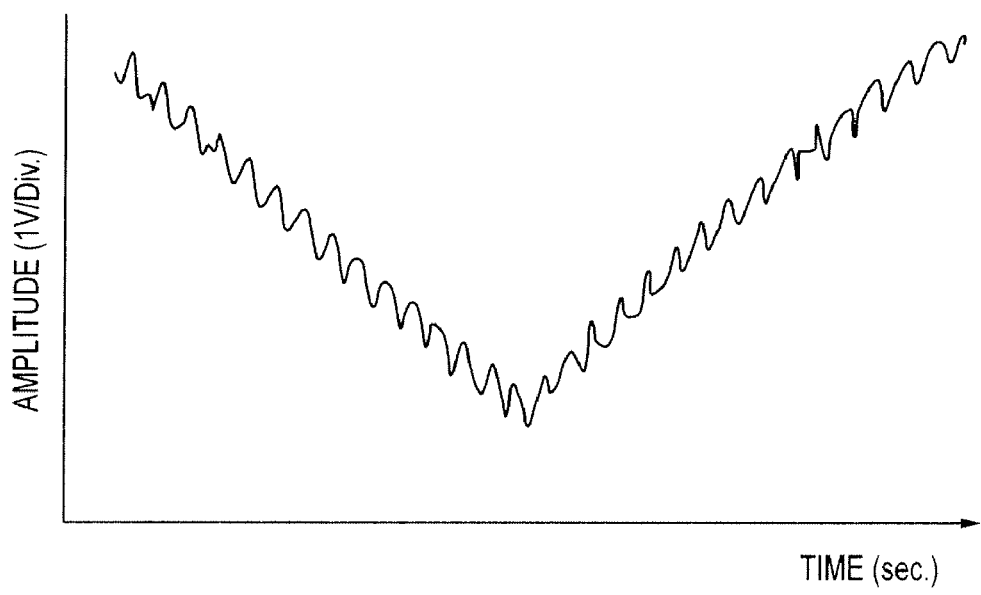

The external field 510 may be generated in any manner to achieve any desired result. For example, the field 510 may be generated by intermixing signals having different characteristics. FIGS. 9 and 10A, display examples of waveforms of the field 510 that may be produced by intermixing frequencies of 7.6 Hz denoted as 810, 71.25 Hz denoted as 820, and 3040 Hz to create one or more dominant intermix frequencies. In the center is a low amplitude time domain 2 second trace. FIG. 10B displays an example of a 3040 Hz signal that may be produced and denoted as 1120. This display is similar to that with the intermix of the 3040 Hz signal with the 7.6 Hz and 70.25 Hz or 71.25 Hz signals. In the example shown in FIG. 9, the dominant intermix frequency is 22.8 Hz. FIG. 9 is in the time domain and 10A and 10B are in the frequency domain. Any number of frequencies in any combination may be utilized in generating the external field 510. FIG. 11, for example, displays a waveform that may be generated by intermixing signals having frequencies of 7 Hz and 70 Hz. Appropriate amplification of the properly operating emitted signal may be achieved in various manners. One such manner is displayed in FIG. 11. In FIG. 11, two signal traces are displayed. The lower amplitude trace displays an emitted signal with no amplification factor and a second signal generated with a factor of about 20 times gain, which is displayed by the higher amplitude trace in this figure. Additionally, multiple frequencies may be intermixed in any appropriate manner, such as by modulating a low frequency with a higher frequency signal in order to carry a suitable amount of information to replace the Fourier frequency components from tissue. Referring now to FIG. 12a, for example, a low-intensity 70 Hz signal may ride on a more-intense, higher-amplitude 7 Hz square wave signal. The frequencies intermixed to generate the field 510 may include any appropriate combination of waveforms. For example, referring now to FIG. 12b, the 70 Hz signal may comprise a square wave, and the 7 Hz signal may comprise a triangle wave.

The field 510 may be provided to patient to achieve any desired result, such as pain measurement and treatment, determining the status of a biologic process, and treatment of a disease. The field 510 may be delivered to a living being in any suitable manner. In one embodiment of the present invention, for example, an electromagnetic field 510 is delivered to a patient by placing one or more inductive coils on or near the surface of the skin producing electromagnetic fields 510 at or near locations associated with the pain in the patient. In another exemplary embodiment, an electrical field 510 is provided to a patient using electrodes attached cutaneously or subcutaneously to the patient. The field 510 may be delivered to any suitable location on the living being in any manner.

Figure 13:
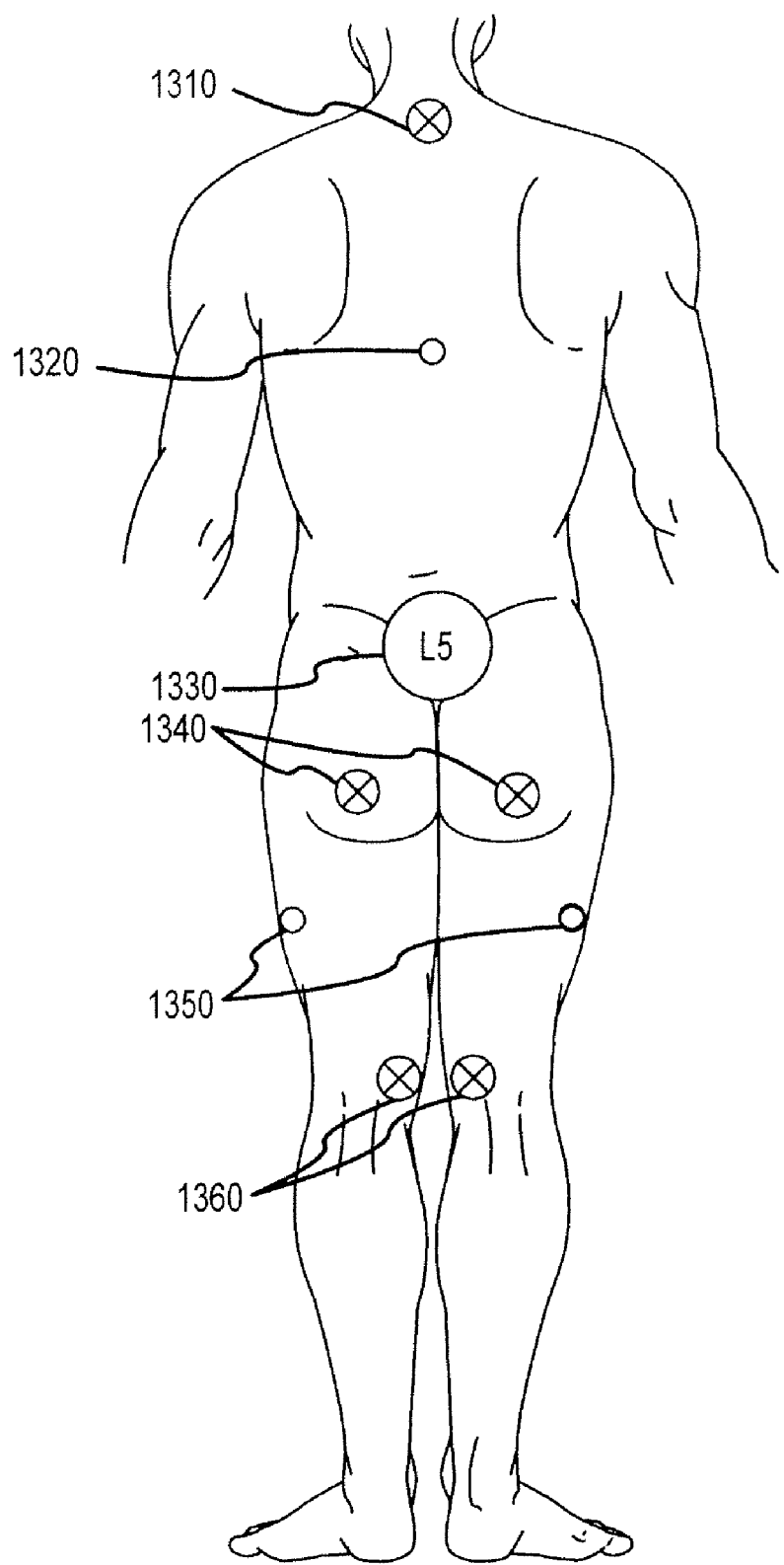
FIG. 13 is a diagram illustrating exemplary locations in which a field may be provided to a patient to treat pain according to various aspects of the present invention.

For example, referring to FIG. 13, electromagnetic fields 510 having positive or negative polarities may be delivered to a patient at multiple locations selected for their association with pain at the T7 and L5 vertebrae in the patient. In this example, the treatment of the pain may be performed in three phases. In the first phase, a solenoid having a positive polarity bias may be placed at or near the patient's C7 vertebrae 1310. Solenoids having a negative polarity bias may be placed at the patient's T7 vertebra 1320 and L5 vertebra 1330, as well as on sciatic injection points 1340. In this exemplary configuration, the first treatment may comprise providing electromagnetic fields 510 of 10 to 15 Gauss to the patient through the solenoids for a period of about 40 minutes. For the second phase of the treatment, the solenoids at the T7 vertebra 1320 L5 vertebra 1330 are removed and electromagnetic fields 510 of 10 to 15 Gauss are provided to the patient through the remaining solenoids for about 20 minutes. For the third phase of the treatment, a positively-biased solenoid is placed at the patient's C7 vertebra 1310 two negatively-biased solenoids are placed on the outside of the thighs 1350 or just above the inside of the patient's knees 1360, and electromagnetic fields 510 are provided to the patient through the solenoids for about 20 minutes at about 10 to 15 Gauss. In this treatment example, electric fields 510 may be provided to the patient using external, cutaneous or subcutaneous electrodes as an alternative to, or in conjunction with, the use of solenoids providing electromagnetic fields 510.

Any number of fields 510 having any appropriate characteristics may be provided to the living being in any manner. In one embodiment of the present invention, for example, a plurality of inductive coils generating electromagnetic fields 510 may be placed at or near various locations of the being. Any number of inductive coils or other devices suitable for delivering the field 510 may be employed in this manner. The characteristics of the fields 510 produced by each coil may be different, for example in order to simultaneously expose the being to fields 510 having a variety of frequency characteristics.

Table 1, depicts exemplary frequencies which can be utilized in conjunction with embodiments of the said invention. Exemplary duty cycles and wave forms are also shown, as well as the external field intensity at the skin surface to activate the associated biologic system which is also listed. These frequencies can be applied in order to effect and normalize and correct biologic processing or to eliminate pain. Some of the time constants for the various exemplary frequencies are described as follows. The 7.6 Hz frequency has a time constant of T=131.6 m sec. and $\tau$=T/2=65.8 m sec (for about a 50% duty cycle) for a bandwidth $f_{BW}$=2/$\tau$=30.4 Hz. The 70.25 Hz frequency, T=14.2 m sec and $\tau$=7.12 m sec for $f_{BW}$=281 Hz and for the 71.25 Hz frequency T=14.0 m sec and $\tau$=7.0 m sec and $f_{BW}$=285 Hz. For the 3040 Hz frequency, T=33 m sec and $\tau$=165 m sec for $f_{BW}$=12.2 kHz. The full 7200 Hz value can be nonlinear related to the 3040 Hz signal for use in the treatment of osteoporosis.

TABLE 1

| Frequency (Hz) | Approximate Bandwidth (Hz) | Approximate Duty Cycle (%) | Dominant But Not Only Wave Form | Approximate Intensity Range (G) | Primary Biologic System |
|---|---|---|---|---|---|
| 7.6 | 30.4 | 50 | Square | 1.5-50 | Cardiac, Iliac Bifurcation, other systems such as the brain connection |
| 70.25 for females 71.25 for males | 281 | 25 | Square | 5-50 | CNS, PNS and other nervous tissues |
| 3040 | 12,160 | 33 | Triangle Ramp Wave | 5-50 | Bone, collagen, connective tissues and neuronal processes, endocrine system |
| Full Wave Value of about 7,200 | 24,320 | 33 | Triangle Ramp Wave | 5-50 | Primarily bone and collagen |

Pain Treatment

The field 510 may be configured and modified in any manner to achieve any desired result. For example, the magnitude of the field 510 may be amplified from a level of about 5 gauss to about 50 gauss or higher in order to effectively eliminate pain in a being. The strength of the field 510 may be amplified or decreased to any level in order to achieve a desired result.

The field 510 may be delivered to a living being as part of a treatment regimen. Any suitable treatment regimen may be used to treat a patient. For example, a method for treating back pain according to various aspects of the present invention may include repeatedly providing an electromagnetic field 510 to locations of a patient's back associated with pain. Such treatments may be employed in conjunction with any other method or process. For example, a patient's pain may be measured before and after each treatment session to gauge the effectiveness of the treatments.

Pain Measurement

Figure 14:
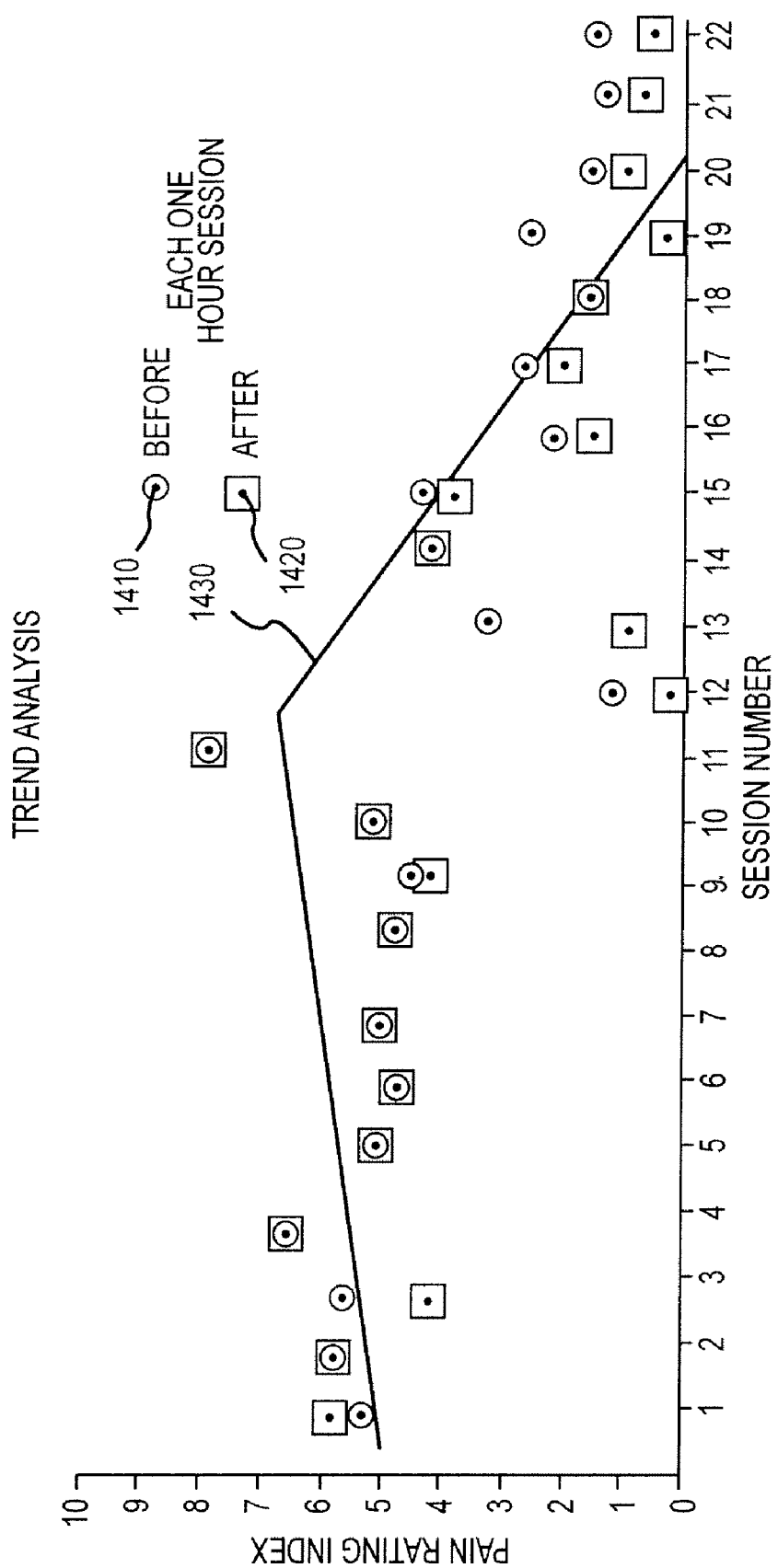
FIGS. 14 and 15 are graphs illustrating the measurement of pain and pain reduction according to various aspects of the present invention.

The field 510 may be delivered to a living being for any other suitable purpose, such as to measure the amount of pain the being is experiencing. Pain may be measured in any suitable manner to achieve any desired result. In one exemplary embodiment of the present invention, pain may be tracked according to a pain-rating index and monitored over a period of time. Referring now to FIG. 14, for example, the pain rating of a patient may be tracked over a period of treatment sessions to determine the effect of the treatment on the patient's pain. In this example, a 59-year-old, Caucasian female experiencing pain in her neck and lower back for 12 years due to an accident. This patient had a long history of drug intake. Numerous therapies, such as physical therapy, massage, chiropractic manipulation, acupuncture, traction, biofeedback, epidural anesthesia, etc. had been administered to this patient without success. Over the period of twenty-two one-hour treatment sessions, the patient's pain rating was measured before 1410 and after 1420 each treatment session and the results plotted. Control treatment session were conducted with the device in the inactive mode with no signal from 520 for sessions 1 through 12. At session 13 denoted as 1430, sessions from 13 to 22 where active, with emitted field 510. The vertical scale is the level of pain experienced by the person which is plotted from zero to ten. The zero reading on the Visual Analog Scale (VAS) goes from zero (which is no pain) to ten (which is the maximum pain experienced by the person). In the range of five to ten, the pain rating level is associated with significant pain that interferes with the quality of life and affects the ability of the person to function normally. The horizontal scale is the session number with several days between sessions. Pain elimination can occur with fewer treatment sessions than depicted in FIG. 14. In this exemplary application of methods of the present invention, the patient experienced a continual decrease in pain as the treatments progressed.

Figure 15:
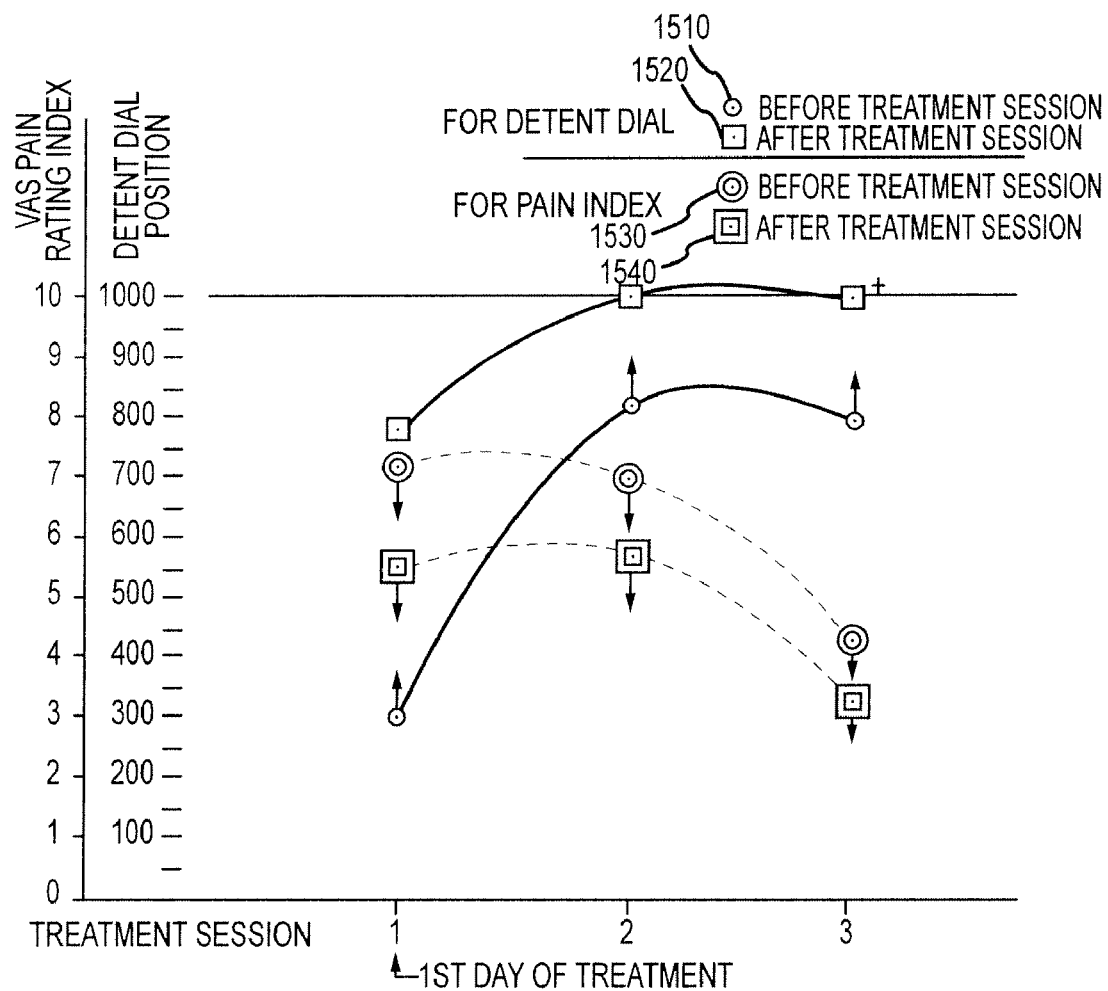

Any suitable scale, process, method, and/or the like for measuring pain may be employed in conjunction with the present invention. In one exemplary embodiment, two or more cutaneous electrical signal emitter electrodes are placed on either side of the region in which one desire to access information on the stimulus tolerance level. The current level is increased until the patent exhibits a startle reaction and reports a sensation of "tingling". As pain decreases in the patient, the current level at which the patient reports the sensation of tingling increases. Readout of the pain measurement can be made in the frequency domain or other appropriate instrumentation utilizing the device of this invention. Blood flow monitoring demonstrates that there is increased flow in lower limbs after treatment with the device of this invention in cases in which the patients had restricted blood flow. Referring to FIG. 15, for example, the pain measurement readings for a patient generated using a device and methods according to various aspects of the present invention may be compared with the patient's pain rating on a Visual Analog Scale (VAS) before and after three sessions of treatment. This data was generated from a patient who was a 47 year old Caucasian male who had a lower back injury and who had not responded to multiple non-surgical and surgical procedures including two laminectomies. He had pain in his lower back and lower legs due to an accident that crushed four lumbar vertebrae and was treated with the device of this invention. In this example, the VAS scale may be plotted along with the corresponding position of a detent dial used to rate the patient's pain level on the pain measurement device. In this example, the position of the detent dial on the pain measurement device is measured before 1510 and after 1520 each treatment session. Similarly, the patient's VAS pain rating is measured before 1530 and after 1540 each session, and the results are plotted together for comparison.

Exemplary Circuit

Figure 16:
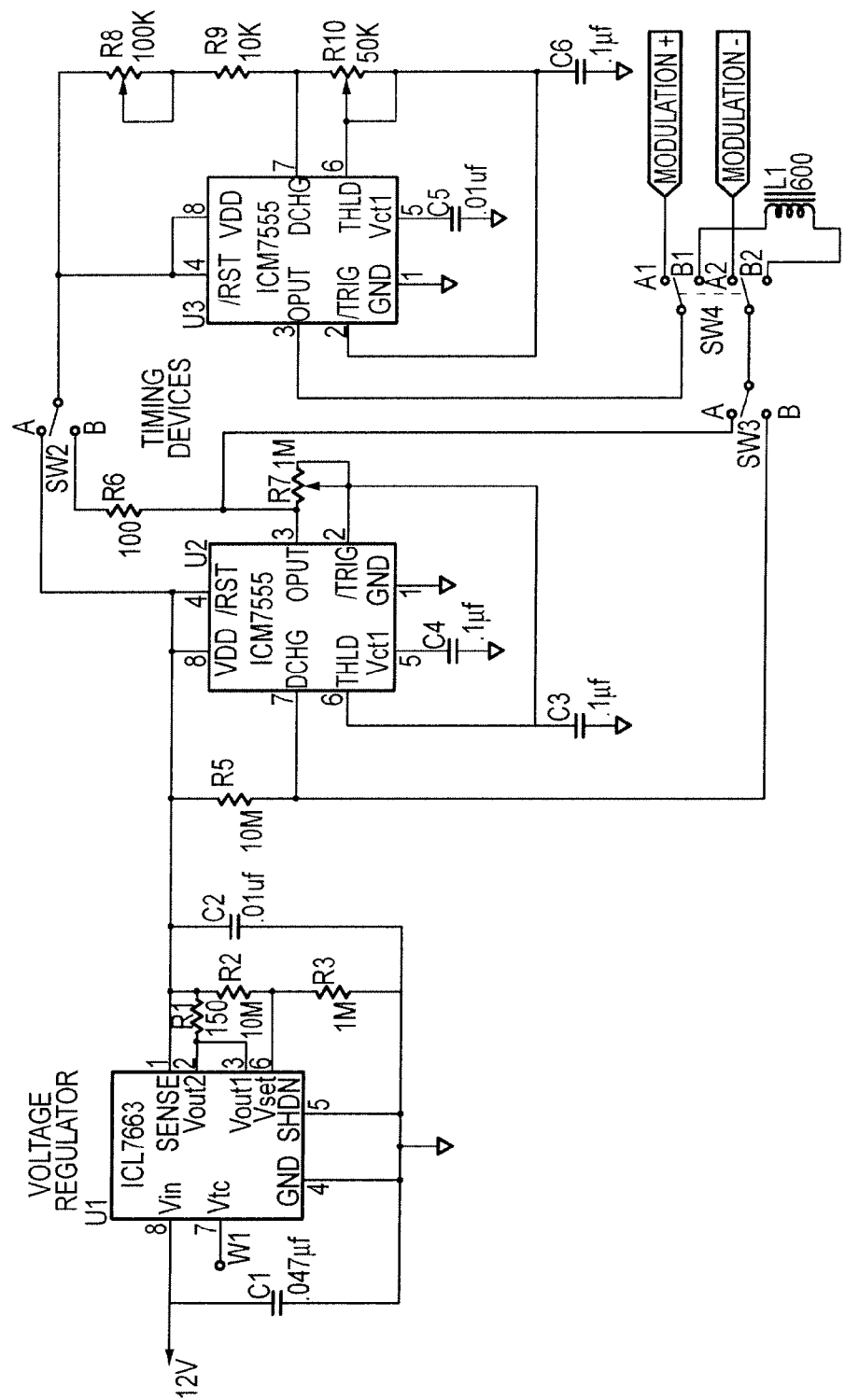
FIGS. 16, 17, and 18 are circuit diagrams depicting portions of devices for pain measurement and treatment according to various aspects of the present invention.
Figure 17:
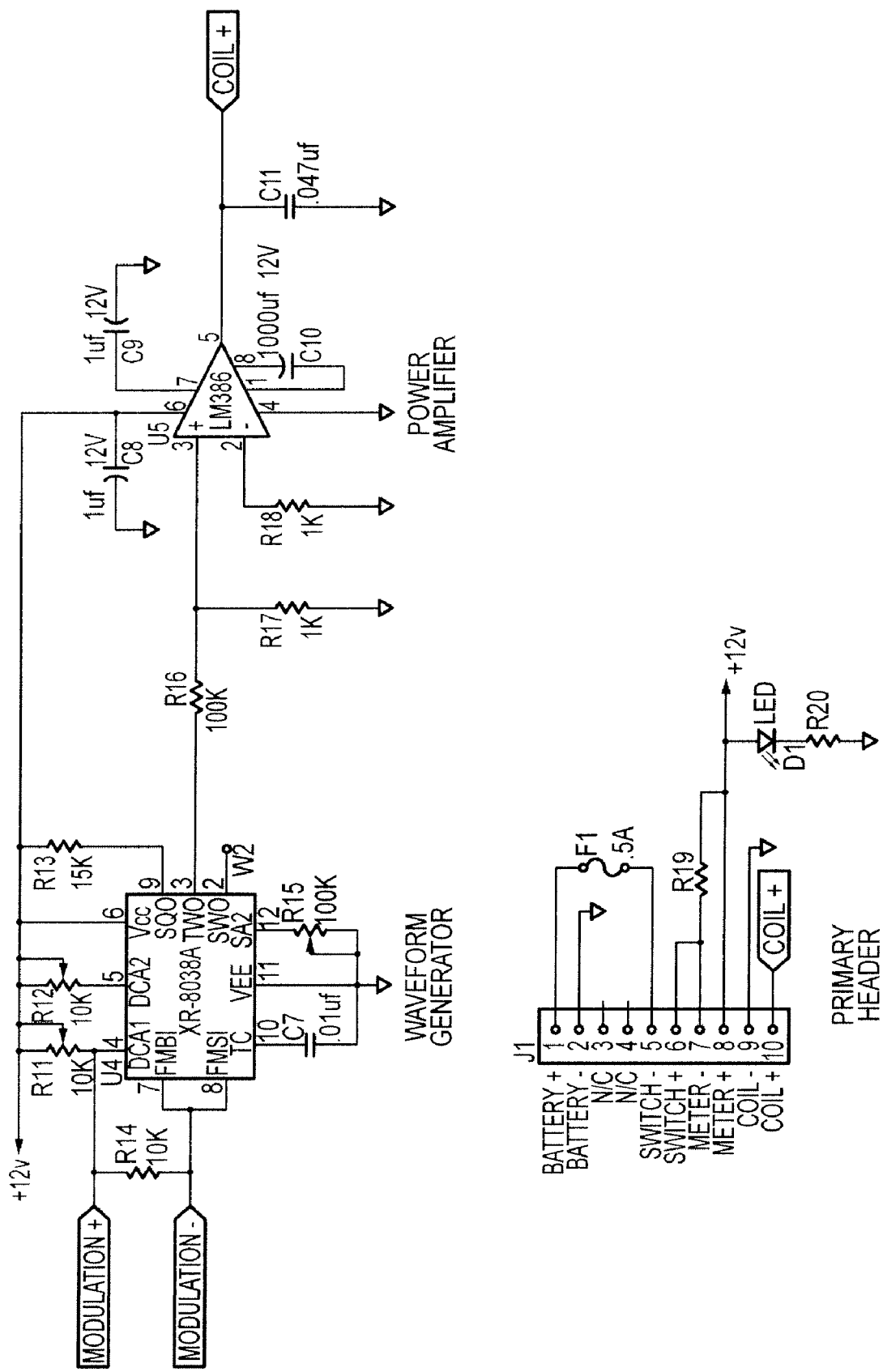
Figure 18:
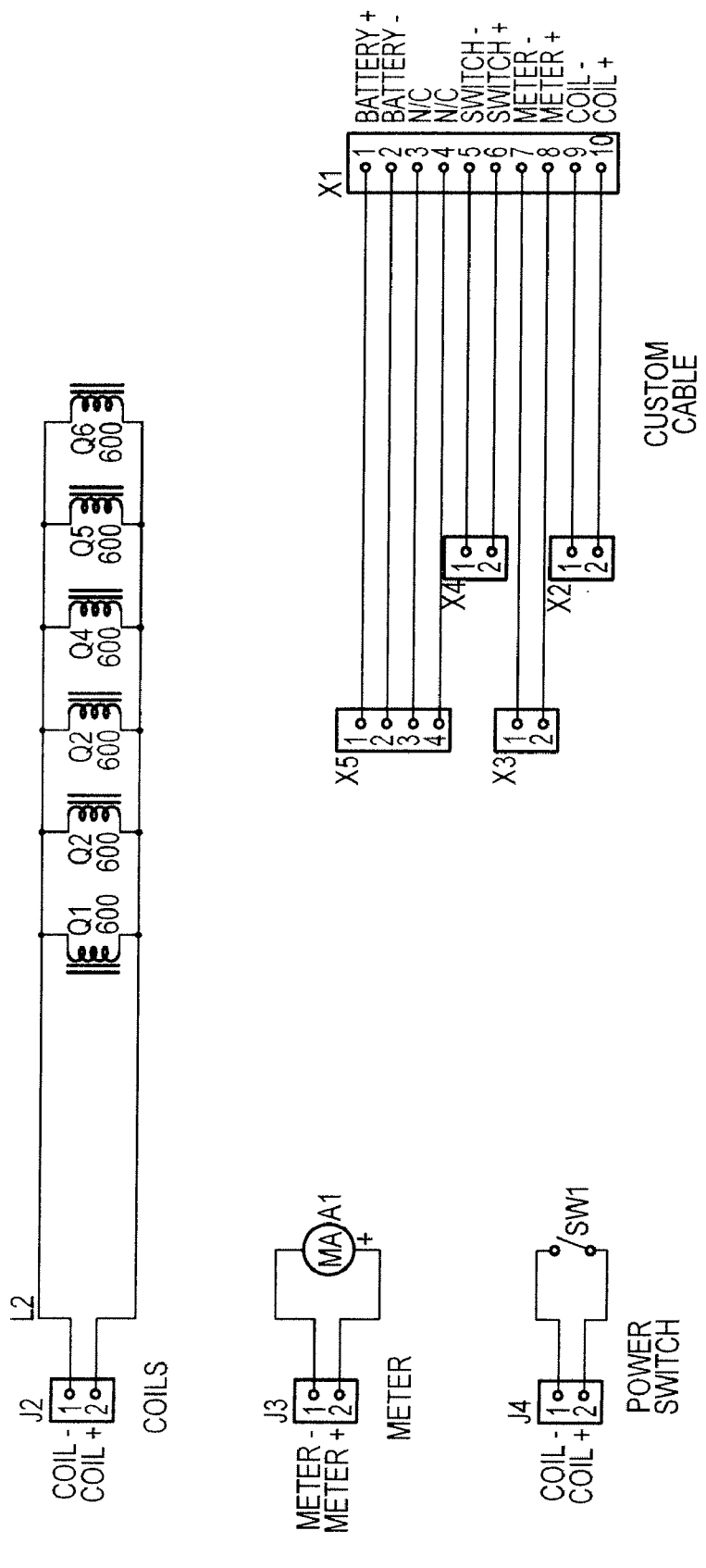

Methods for pain measurement and treatment according to various aspects of the present invention may be implemented in any suitable manner, such as through the use of an electronic circuit. The circuit may be configured to generate any number of currents having any appropriate characteristics. An exemplary circuit that may be employed with methods for treating and measuring pain according to various aspects of the present invention is depicted in FIGS. 16, 17, and 18. This exemplary circuit may include a battery B1 supplying power through a voltage regulator U1 to one or more timing devices U2, U3, which in turn generate signals to be intermixed by a waveform generator U4 and provided to one or more coils L2 to generate electromagnetic fields 510. This exemplary circuit also includes a meter A1, power switch SW1, and cable connector assemblies X1-X5. The circuit may operate in conjunction with any other suitable devices. For example, the circuit may interface with a decode counter device to indicate length of treatment times with an appropriate display (not shown).

The values and configuration of the components in these figures are exemplary, and components of any appropriate configuration and value may be employed to implement aspects of the present invention. Additionally, the types of components described are not intended to limit the present invention to any particular implementation, and any other appropriate components may be substituted and utilized. The values and characteristics of various components may be selected according to any suitable criteria. For example, referring to FIG. 17, the capacitance of capacitor C10 connected to amplifier U5 may be selected to account for the variability of biologic processes in a living being.

The voltage regulator U1 may comprise any suitable devices for regulating power, such as an Intersil ICL7663 voltage regulator. When a first switch SW1 is closed, power from the battery B1 is supplied to the voltage regulator U1, which in turn controls the voltage of the power supplied to the rest of the circuit. Capacitor C1 may be connected to pin 8 (Vin) of U1 prevents power spikes. Current-limiting resistor R1 is connected to Vout pins 2 and 3, and then to a voltage divider network comprising resistors R2 and R3 and divided by a connection to pin 6 (Vset) of U1. Capacitor C2 is connected in parallel to the voltage divider network to prevent power spikes. The voltage output of the voltage regulator U1 is connected to resistor R5 which is connected to the output terminal 7 (DCHG) of timer U2 and to one pole of a switch SW3. The voltage output of the voltage regulator U1 is also connected to pins 8 (VDD) and 4 (/RST) of timer U2 and to switch SW2.

The timing devices U2, U3 may be configured to generate a signal having a specific frequency. Any suitable device for generating a signal at a specified frequency may be used, such as an Intersil ICM7555 or ECM7555. Such devices may be utilized to generate a signal having any suitable waveform with any desired duty cycle, such as a square wave with a duty cycle of about 50 percent. In the exemplary embodiment of the present invention illustrated in FIG. 16, the frequency and duty cycle of the signal produced by timer U2 is selected using a timing capacitor C3 and variable resistor R7 connected to pin 6 (THLD), pin 3 (OPUT) and pin 2 (/TRIG). One output from pin 7 (DCHG) is connected to the junction of resistor R5 and Pole B of switch SW3. A second output from pin 3 (OPUT) leads through resistor R6 to switch SW2. Pin 3 (OPUT) of U2 is also connected to pole A of SW3. The resistance of variable resistor R7 may be modified to cause timer U2 to generate a signal having any desired frequency and duty cycle. In this exemplary embodiment generate a signal of about 7 Hz with a duty cycle of 50 percent.

Switch SW2 controls the input to timer U3. Any switching mechanism may be used in conjunction with any appropriate input source. In this exemplary embodiment, SW2 comprises a single-pole-double-throw (SPDT) switch used to select between the output of the voltage regulator U1 and the signal generated by timer U2. The input selected by switch SW2 is provided to timer U3 at pin 4 (/RST) and pin 8 (VDD). The input selected by switch SW2 is also provided to variable resistor R8, which is connected in series to resistor R9, variable resistor R10, and timing capacitor C6. Resistor R9 and variable resistor R10 comprise a voltage divider bisected by a connection to pin 7 (DCHG) or timer U3. A signal having any desired frequency and duty cycle may be produced by timer U3 by modifying the resistances of variable resistors R8 and R10. In one embodiment of the present invention, for example, the resistances of variable resistors R8 and R10 may be modified to produce a signal of about 70 Hz at a duty cycle of 50 percent.

Switch SW2 may operate in conjunction with any other type of switching device, such as double-pole-double-throw (DPDT) Switch SW3. In this exemplary embodiment, when switches SW2 and SW3 are in the "B" position, the 7 Hz signal generated by timer U2 and the 70 Hz signal generated by timer U3 are connected to a coil L1 to produce an electromagnetic field 510. Coil L1 may comprise any number of solenoids and other devices configured to deliver a field 510 to a patient, such as electrodes. Referring to FIGS. 16 and 17, when switches SW2 and SW3 are in the "A" position, the signal outputs from timers U2 and U3 are provided to signal generator U4.

Signal generator U4 utilizes the signals generated by timers U2 and U3 to generate a back ramp wave 3040 Hz signal according to aspects of the present invention. Signal generator U4 may comprise any suitable device or combination of devices, such as an Exar XR-8038A precision waveform generator. The signal generator U4 may operate in conjunction with any other devices, such as an amplifier U5.

The signal produced by signal generator U4 may configured in any manner. For example, the duty cycle of the signal may be configured by modifying the inputs to pin 4 (DCA1) and pin 5 (DCA2) using variable resistors R11 and R12, respectively. In this exemplary embodiment of the present invention, the signal from timer U3 is provided to pin 4 (DCA1) of U4, while the signal from timer U2 is provided to pin 7 (FMBI) and pin 8 (FMSI). The outputs from U2 and U3 are connected via a resistor R14. A switching mechanism (not shown) may be placed between the outputs from timers U2 and U3 to, for example, select between the inputs to be provided to signal generator and/or to provide additional signals to the signal generator U4. The wave form produced by the signal generator U4 may also be configured by modifying the resistance of variable resistor R15, which is connected along with timing resistor C7 to pin 10 (TC), pin 11 (VEE) and pin 12 (SA2) as shown in FIG. 17.

The outputs of the signal generator U4 may be utilized in any appropriate manner. In the present exemplary embodiment, the square-wave output from pin 9 (SQO) is provided to amplifier U5 through a resistor R13. Additionally, the triangle-wave output from pin 3 (TWO) is also provided to the amplifier U5 through R16. The amplifier U5 may comprise any suitable signal amplifier, such as an LM386 Low Voltage Audio Power Amplifier from National Semiconductor. The pins of amplifier U5 may be connected to the signal generator U4 and other components as shown in FIG. 17. Pin 1 of U5 is connected through a capacitor C10 to pin 8. Pin 2 of amplifier U5 is connected though resistor R18 to ground. Pin 4 of the amplifier U5 is connected to ground. Pin 7 is connected through capacitor C9 to ground. Referring to FIGS. 17 and 18, the amplified signal from the amplifier U5, pin 5, provides one input to a bank of coils L2, and is also connected to ground through a surge-suppressing capacitor C1. The input to the coils L2 in the present exemplary embodiment comprises a 3040 Hz signal having a 33 percent duty cycle. The 3040 Hz signal is generated by modulating the 7.6 Hz signal having a 50% duty cycle from timer U2 with an approximately 70 Hz, 25% duty cycle pulse signal from timer U3. The 3040 Hz intermix signal may have any other appropriate characteristics. For example, the signal may be configured to deliver approximately one ampere of current to a coil assembly L2 having a one hundred ohm load. The amplifier may be employed to achieve any other desired result, such as to amplify the 3040 Hz signal to a sufficient level to generate a field 510 sufficient to provide an anesthetic effect to a portion of a living being.

The assembly of coils L2 depicted in FIG. 18 may include any number of coils in any configuration. For example, a coil assembly L2 may comprise a reference coil Q1 having a positive polarity bias and five coils Q2-Q6 having a negative polarity bias connected in parallel. Any suitable coil may be employed, such as a coil having a μ-metal core and comprising sufficient windings of about AWG #36-44 wire to provide an appropriate inductance and resistance load. The coil may be of any shape. For example, the coil may have a core configured to focus and amplify the magnetic field 510 it generates in order to project the field 510 into the tissue of a living being. The coils Q1-Q6 may have any suitable core composition, such as a μ-metal core of high permeability and low DC resistivity comprising iron, cobalt, nickel, chromium, niodinum, copper, carbon, and/or any other suitable material.

The coil assembly L2 generates one or more electromagnetic fields 510. The coil assembly may produce fields 510 of any strength. In the present exemplary embodiment, the coil assembly L2 produces a moving or dynamic field 510 of anywhere between 0.1 Gauss to over 55 Gauss. Additionally, a circuit according to aspects of the present invention may employ electrodes for delivering an electric field 510 to a living being in concert with, or alternative to, the assembly of coils L2. The circuit may include and/or operate in conjunction with any other suitable system, device, and structure for delivering a field 510 to the patient.

Exemplary Circuit Operation

In one example of the operation of the circuit depicted in FIGS. 16, 17, and 18, timer U2 is configured to produce a 7 Hz signal, while timer U3 is configured to produce a 70 Hz signal. In this example, both signals comprise square waveforms having 50 percent duty cycles. The signals generated by U2 and U3 are provided to the signal generator U4, which combines the two signals to generate a 3040 Hz intermix signal. The 3040 Hz square-wave and triangle-wave signals from the signal generator U4 are combined and amplified by amplifier U5 to produce a 3040 Hz intermix signal having a forward-leaning-ramp and/or sawtooth waveform. The output signal from amplifier U5 is provided to an assembly of one or more coils L2 which generate electromagnetic fields 510 based on the 3040 Hz intermix signal and are provided to a living being to treat and measure pain according to aspects of the present invention discussed previously.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiment without departing from the scope of the present invention. These and other changes or modifications are intended to be included within the scope of the present invention, as expressed in the following claims.

What is claimed is:

1. A method for measuring pain in a living being comprising:
    inducing a perception of pain in a portion of the living being, in a manner that is accompanied by a physiological response, by providing a magnitude of an external field to the portion, wherein the external field comprises a plurality of frequencies including a first frequency of about 3040 Hz, and at least one additional frequency selected from the group consisting of 7.2 to 7.75 Hz and 72 to 77.5 Hz; and
    determining a pain level for the being, comprising:
    modifying the magnitude of the external field; and
    determining the pain level for the being based on a reaction of the being to the step of modifying the magnitude of the external field.

2. The method of claim 1, wherein the external field comprises at least one of a magnetic field and an electric field.

3. The method of claim 1, wherein the additional frequency is about 7.6 Hz.

4. The method of claim 1, wherein the additional frequency is selected from the group consisting of about 70.25 Hz and about 71.25 Hz.

5. The method of claim 1, wherein the external field includes at least one waveform.

6. The method of claim 5, wherein the at least one waveform includes at least one of a triangle wave and backwards ramp wave.

7. The method of claim 5, wherein the at least one waveform includes a duty cycle of 33%.

8. The method of claim 1, wherein determining the pain level for the being further comprises:
    measuring an emitted field from the being; and
    determining the pain level based on the measurement of the emitted field.

9. A method for reducing pain in a living being comprising:
    providing an external field to a portion of the living being in a manner sufficient to reduce a perception of the pain, in a manner that is accompanied by a physiological response,
    wherein the external field comprises a plurality of frequencies including a first frequency of about 3040 Hz, and at least one additional frequency selected from the group consisting of 7.2 to 7.75 Hz and 72 to 77.5 Hz.

10. The method of claim 9, wherein the external field comprises at least one of a magnetic field and an electric field.

11. The method of claim 9, wherein the additional frequency is about 7.6 Hz.

12. The method of claim 9, wherein the additional frequency is selected from the group consisting of about 70.25 Hz, and about 71.25 Hz.

13. The method of claim 9, wherein the external field has a sufficient magnitude to correct a bioelectric signal to reduce the pain.

14. The method of claim 9, wherein the external field has a sufficient magnitude to replace a Fourier frequency component missing from an emitted neuronal pathway field from the being to reduce the pain.

15. The method of claim 9, wherein the external field has a magnitude sufficient to intermix with a signaling mechanism in the being to reduce the being's perception of the pain.

16. The method of claim 9, wherein the external field has a magnitude sufficient to stimulate the being to produce a biochemical that reduces the being's perception of the pain.

17. The method of claim 16, wherein the biochemical comprises at least one of an endorphin, an enkephalin, and a prostaglandin.

18. A device for treating pain in a living being comprising:
    a circuit configured to produce an external field and provide the external field
    to a portion of the living being in a manner sufficient to treat the pain, wherein the external field comprises a plurality of frequencies including a first frequency of about 3040 Hz, and at least one additional frequency selected from the group consisting of 7.2 to 7.75 Hz and 72 to 77.5 Hz.

19. The device of claim 18, wherein the circuit is further configured to vary a magnitude of the external field.

20. The device of claim 18, wherein the external field comprises a magnetic field.

21. The device of claim 20, further comprising a coil that takes part in producing the magnetic field.

22. The device of claim 20, further comprising a plurality of coils that take part in producing the magnetic field.

23. The device of claim 18, wherein the external field comprises an electric field.

24. The device of claim 23, further comprising an electrode that takes part in producing the electric field.

25. The device of claim 18, wherein the additional frequency is about 7.6 Hz.

26. The device of claim 18, wherein the additional frequency is selected from the group consisting of about 70.25 Hz, and about 71.25 Hz.

27. The device of claim 18, wherein the external field has a sufficient magnitude to replace a Fourier frequency component missing from an emitted neuronal pathway field from the being to reduce the pain.

28. The device of claim 18, wherein the external field has a magnitude sufficient to intermix with a signaling mechanism in the being to reduce the being's perception of the pain.

29. The device of claim 18, wherein the external field has a magnitude sufficient to stimulate the being to produce a biochemical that reduces the being's perception of the pain.

30. The device of claim 29, wherein the biochemical comprises at least one of an endorphin, an enkephalin, and a prostaglandin.

31. A method for treating and reducing osteoporosis in a living being comprising:
    applying an external field to a portion of the living being sufficient to treat the
    osteoporosis, wherein the external field comprises a plurality of frequencies including a first frequency of about 3040 Hz, and at least one additional frequency selected from the group consisting of 7.2 to 7.75 Hz and 72 to 77.5 Hz; and
    wherein applying the external field induces physiological changes in the living being.

* * * * *